United States Patent [19]

Haidinger et al.

[11] Patent Number: 5,505,904
[45] Date of Patent: Apr. 9, 1996

[54] AIR DISINFECTION UNIT

[75] Inventors: Robert N. Haidinger, Riverside; Heinz K. Filzer, Brookfield; Tobias A. Brown, Greenwich, all of Conn.

[73] Assignee: JJI Lighting Group, Inc., Greenwich, Conn.

[21] Appl. No.: 235,645

[22] Filed: Apr. 29, 1994

[51] Int. Cl.⁶ ............................................. A61L 9/20
[52] U.S. Cl. .................... 422/24; 422/4; 422/121; 250/435
[58] Field of Search ................. 422/4, 24, 121, 422/186.3; 250/435, 492.1; 55/279; 96/16

[56] References Cited

U.S. PATENT DOCUMENTS

| | | | |
|---|---|---|---|
| 1,553,098 | 9/1925 | Napier | 422/121 |
| 2,347,954 | 5/1944 | Kiely | 422/24 |
| 2,533,690 | 12/1950 | Raider | 422/121 |
| 2,732,501 | 1/1956 | Blaeker | 422/4 |
| 3,011,230 | 12/1961 | Potapenko | 422/121 |
| 3,105,733 | 10/1963 | Potapenko | 422/121 |
| 3,757,495 | 9/1973 | Sievers | 422/24 |
| 3,827,862 | 8/1974 | Berlant | 422/121 |
| 3,846,072 | 11/1974 | Patterson | 422/121 |
| 4,118,191 | 10/1978 | Böhnensieker | 422/121 |
| 4,210,429 | 7/1980 | Golstein | 422/24 |
| 5,112,370 | 5/1992 | Gazzano | 422/121 X |
| 5,225,167 | 7/1993 | Wetzel | 422/24 X |

Primary Examiner—Robert J. Warden
Assistant Examiner—Theresa T. Snider
Attorney, Agent, or Firm—Fitzpatrick, Cella, Harper & Scinto

[57] ABSTRACT

An air disinfection method and unit are disclosed in which air is passed through a housing from an air inlet to an air outlet opening at a predetermined air flow rate under substantially uniform cross-sectional air flow conditions across closely spaced UV-C irradiation lamps located at a distance of between 2 to 4 inches O. C. with the lamps being positioned directly in the air stream so that all air flows passed the bulbs at a distance of not more than 2–3 inches. The bulbs produce UV-C irradiation at a wave length of about 254 nm and have an intensity of about 142 $\mu W/cm^2$. The housing has a predetermined volume selected such that airborne bacteria remain in the enclosure for a residence time of between 0.5 and 1.5 seconds.

42 Claims, 11 Drawing Sheets

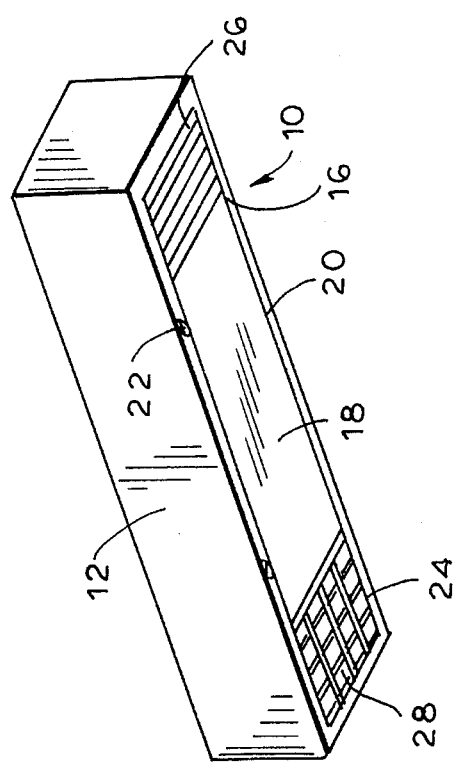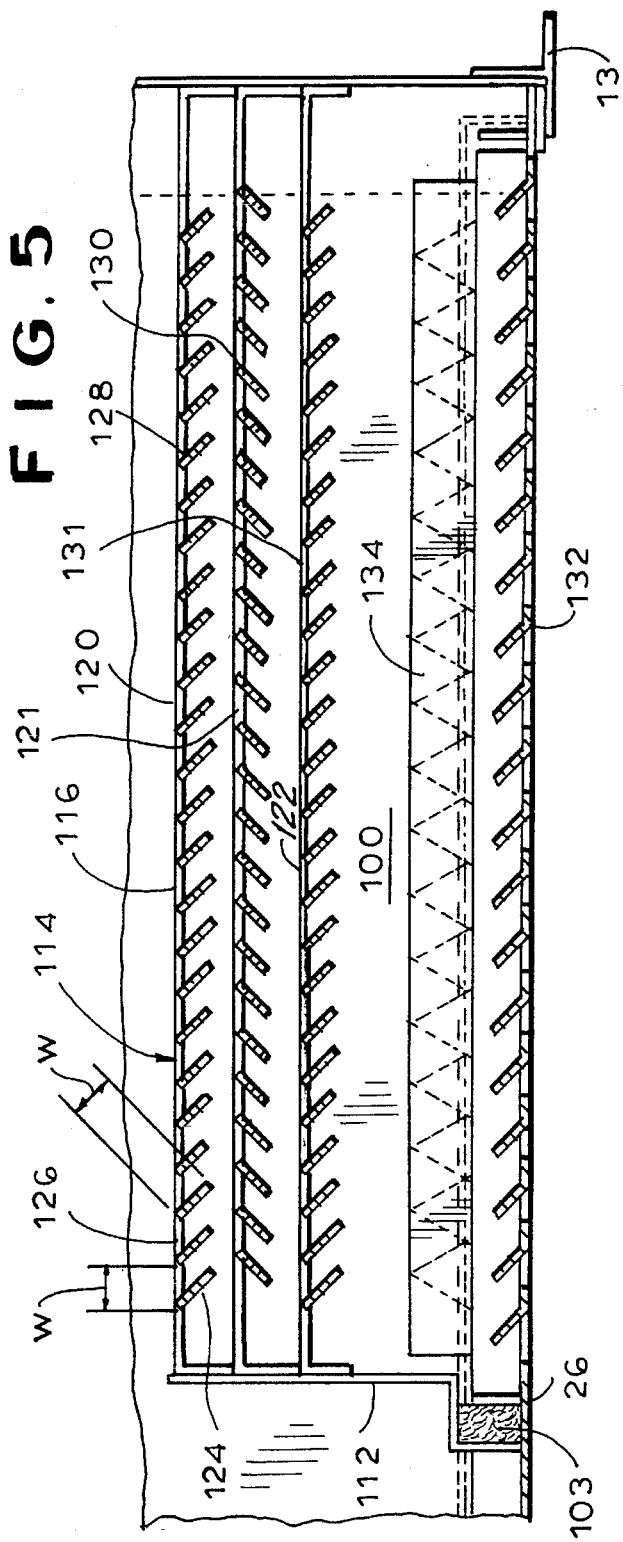

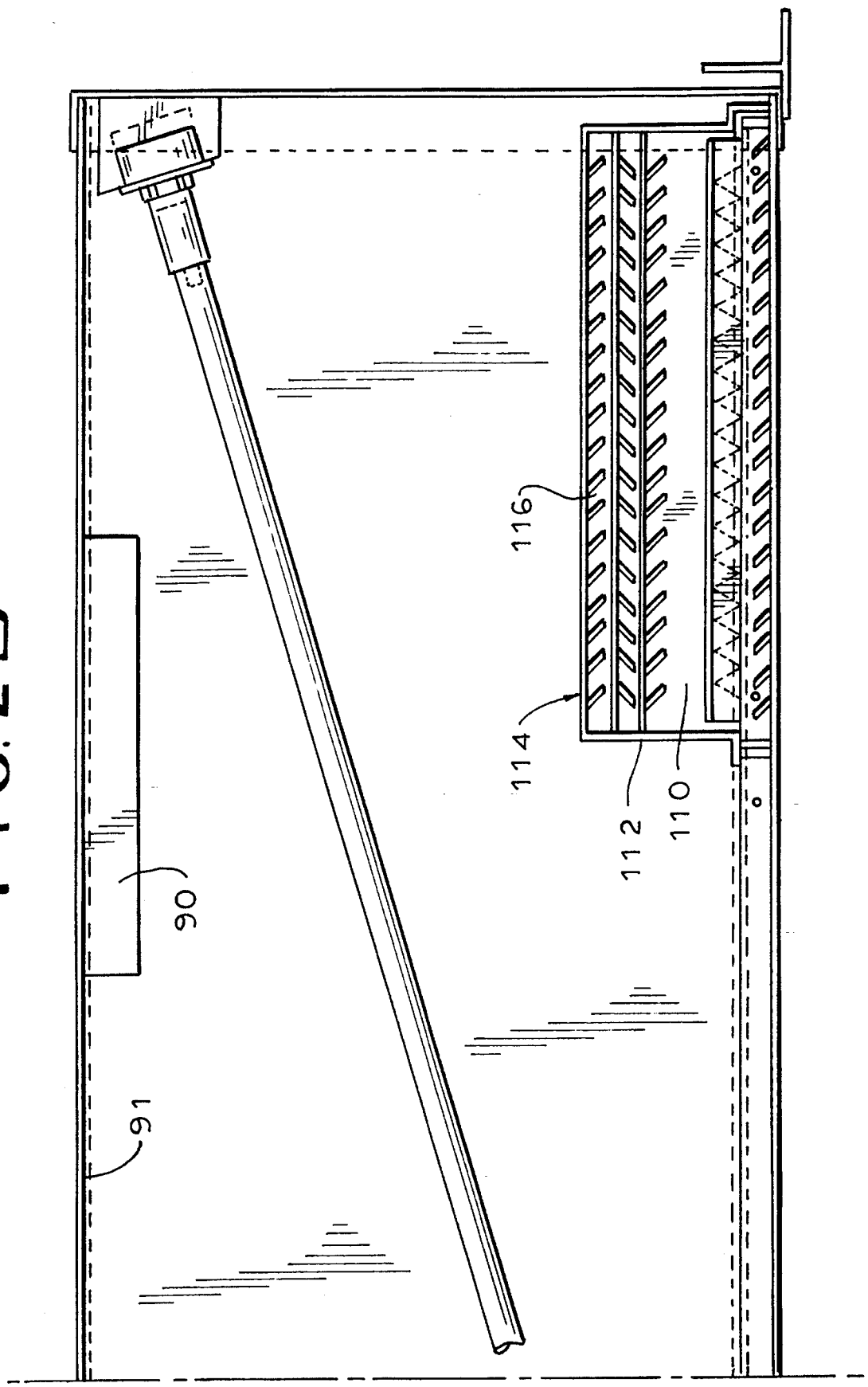

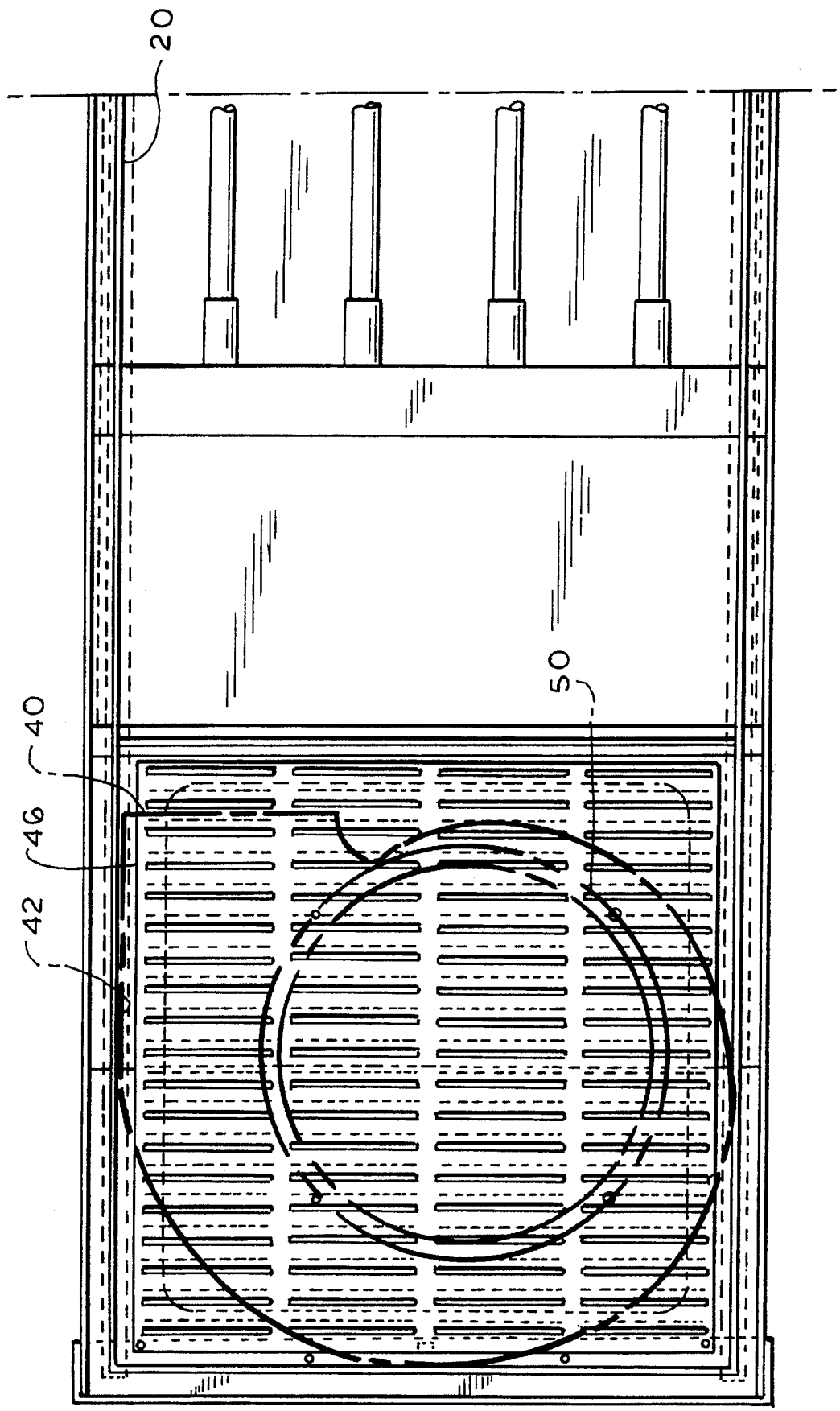

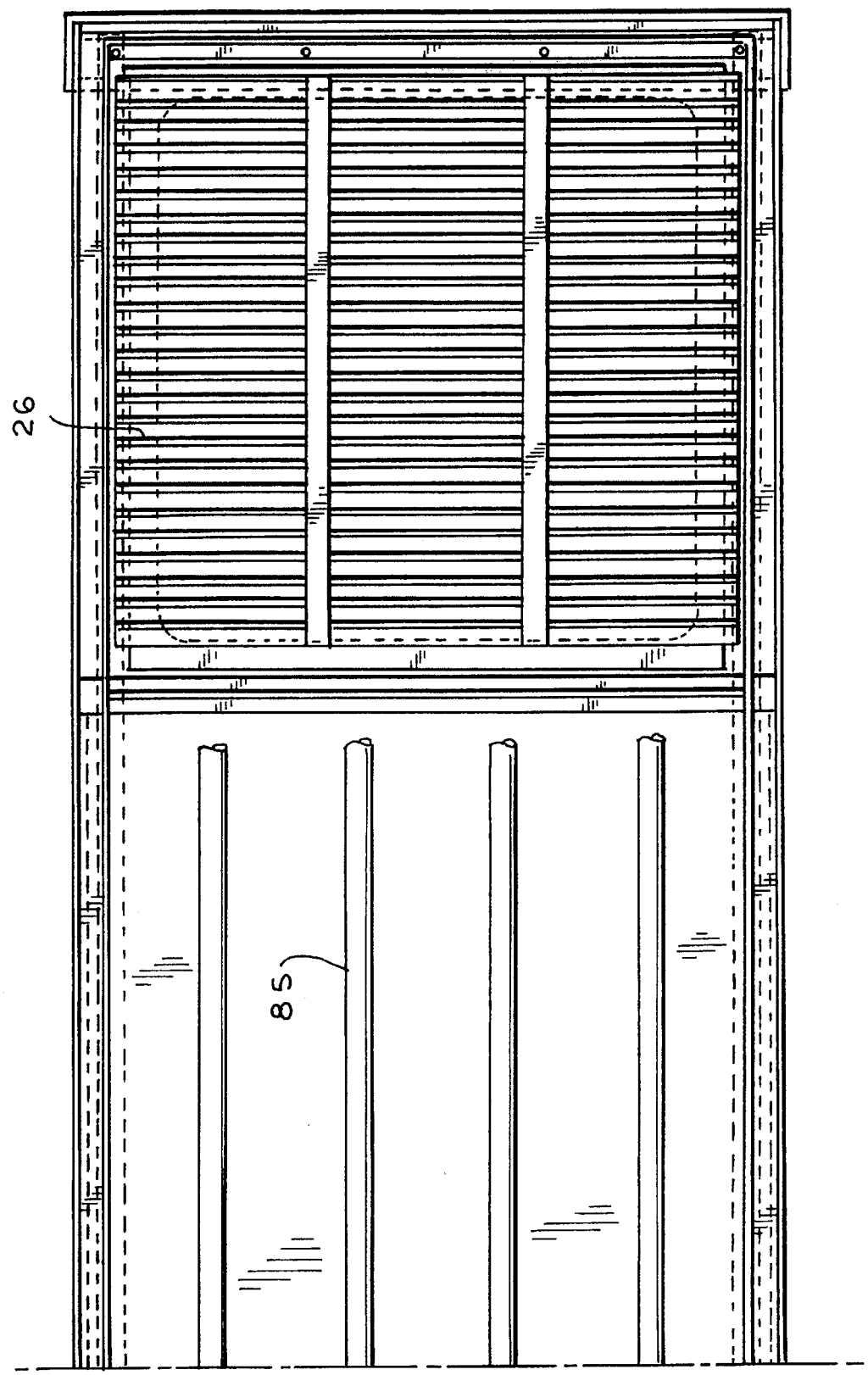

AIR DISINFECTION UNIT

BACKGROUND OF THE INVENTION

1. Field of the Invention

The present invention relates to an air disinfection unit, and more in particular to a fixture using ultra violet irradiation for air disinfection.

2. Background of the Invention

It is well known in the art to use ultra violet irradiation, particularly UV-C irradiation, for air disinfection purposes. Many such devices have been proposed in the prior art. However, none of the prior art devices have achieved any substantial success.

It is an object of the present invention to provide an improved ultra violet irradiation device for room air disinfection.

Another object of the present invention is to provide an ultra violet irradiation device for room air disinfection which is relatively simple in construction yet efficient in use.

Another object of the invention is to provide an ultra violet irradiation unit which has a high disinfection rate.

A still further object of the present invention is to provide an ultra violet irradiation unit which is adapted to be mounted in the ceilings of rooms for unobtrusive operation.

BRIEF DESCRIPTION OF THE INVENTION

In accordance with an aspect of the present invention an air disinfection unit is provided which includes a housing having air inlet and air outlet openings formed therein. A blower is provided in the housing for passing air through the housing from the air inlet to the air outlet opening at a predetermined flow rate. UV-C irradiation lamps are positioned in the housing between the air inlet and air outlet openings in order to disinfect air flowing therethrough. The lamps are located in closely spaced relationship to each other at a distance of between 2 inches to 4 inches on center (hereinafter "O. C."). The light producing portions of the lamps are positioned directly in the air stream produced by the blower so that air flows passed the lamps at a distance of no more than about 2 inches. In addition means are provided in the housing for creating uniform air flow across the cross section of the housing through the lamps to enhance the effectiveness of the lamps in disinfecting bacteria in the air stream. The lamps produce UV-C irradiation at a wavelength of about 254 nm and have an intensity of about 142 $\mu W/cm^2$ measured at one meter in a black box. The enclosure is designed with a predetermined volume selected such that airborne bacteria remain in the enclosure during operation of the blower for a residence time of between 0.5 and 1.5 seconds.

The disinfection unit of the present invention has been shown to effectively inactivate airborne bacteria. In one embodiment of the invention the unit has a dimension of 1' in height, 1' in width and 4' in length. Such a unit contains 4 ultra violet lamps located in the air stream. Test results on such units indicate a mean inactivation rate of bacteria such as *Escherichia coli, Pseudomonas fluoresces, Serratia marcescens, Micrococcus luteus* and *Bacillus subtilis* of 99.52%, without any filtration. When a filter was used with the device mean inactivation rates of 99.81% of such bacteria were experienced. It is believed that these inactivation rates far exceed inactivation rates of any previously proposed UV disinfectant unit.

The above, and other objects, features and advantages of this invention, will be apparent in the following detailed description of illustrative embodiment thereof, which is to be read in connection with the accompanying drawings, wherein:

BRIEF DESCRIPTION OF THE DRAWINGS

FIG. 1 is a schematic perspective view of a disinfectant unit constructed in accordance with one embodiment of the present invention constructed to be located in a dropped ceiling;

FIGS. 2A and 2B are a side sectional view of the unit shown in FIG. 1;

FIGS. 4A and 4B are a bottom view of the unit shown in FIG. 1 with the bottom closure door removed;

FIG. 5 is an enlarged sectional view of the light trap and exit air filter shown in FIG. 2B;

DETAILED DESCRIPTION

Figure 2A:
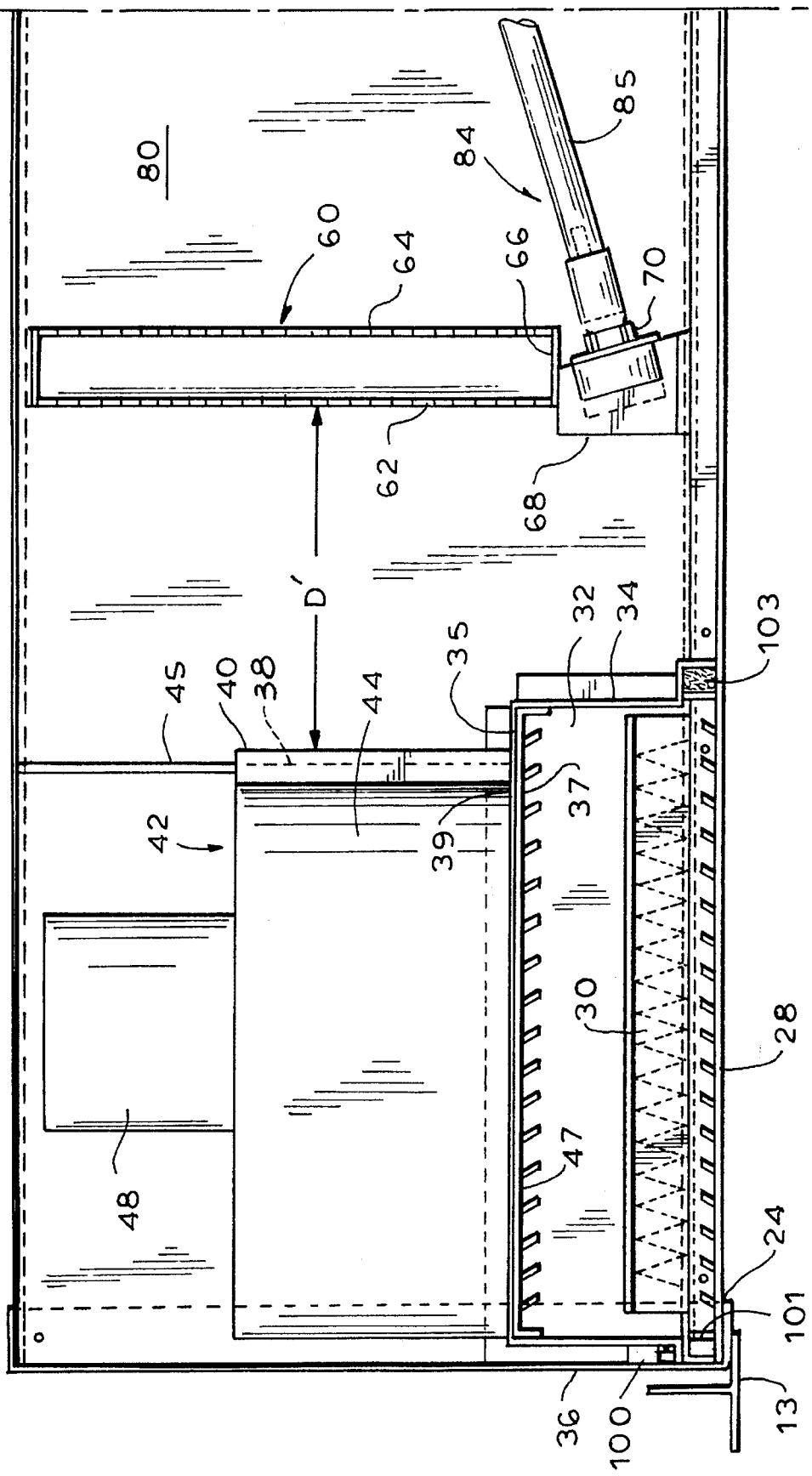
Figure 3:
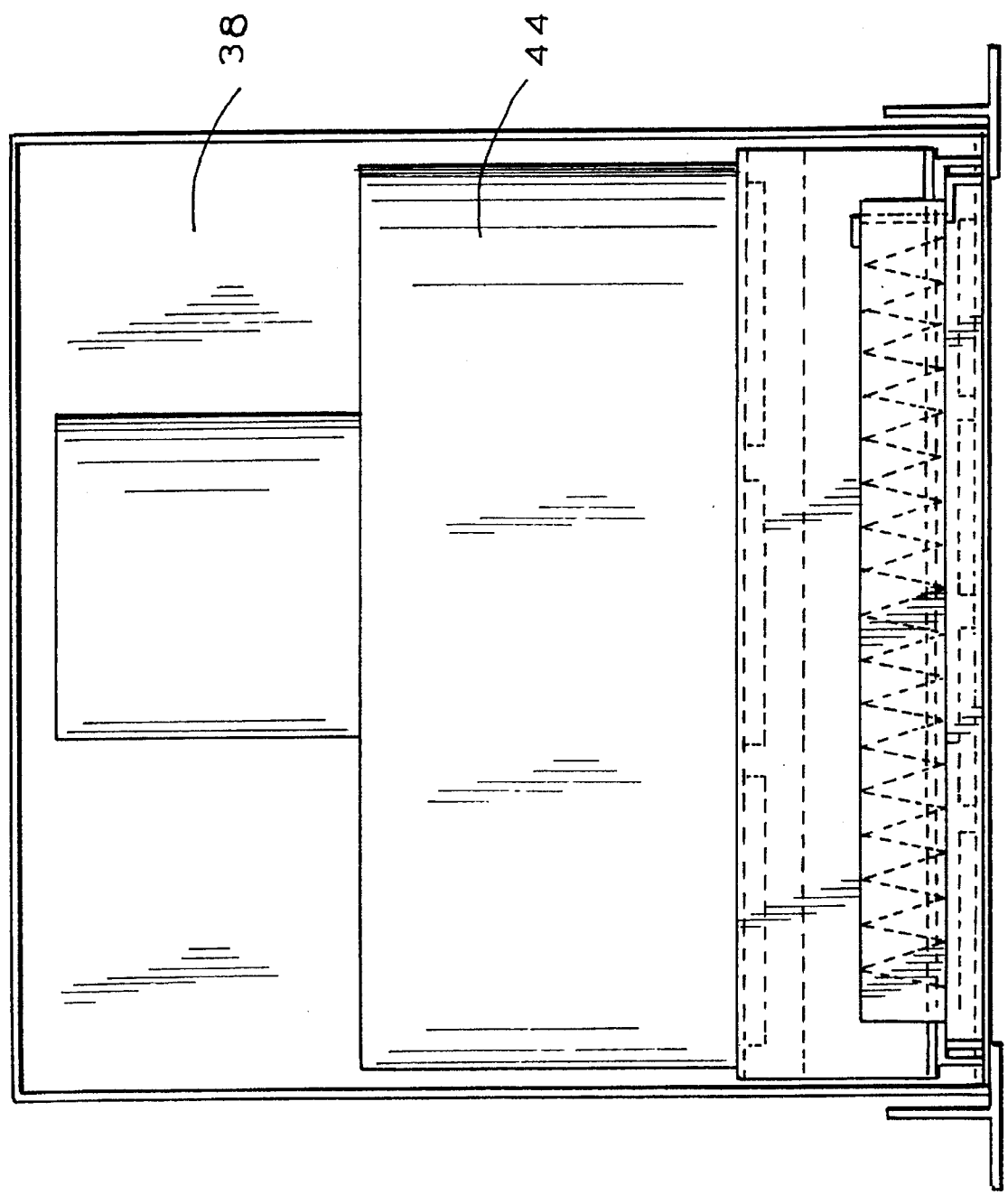
FIG. 3 is an end sectional view of the unit shown in FIG. 1; taken along line 3—3 in FIG. 2A.

Referring now to the drawing in detail, and initially to FIG. 1 thereof, a disinfection unit 10 constructed in accordance with the present invention is illustrated. Unit 10 includes a housing 12 which, in the illustrative embodiment of the invention, is 1' wide, 1' in height, and 4' long. The one foot width is selected so that the unit can conveniently fit in a false or dropped ceiling in a manner similar to that of a conventional ceiling light fixture. As illustrated schematically in FIG. 2a housing 12 is conveniently supported on the support T's 13 of the dropped ceiling construction.

Housing 12 includes a lower access opening 16 which is closed by a door 18. The door 18 is preferably hinged in any conventional manner to the housing along one edge 20 thereof (see FIG. 4) with conventional latching members or screws 22 at the opposite edge of the device for securing the door in its closed position thereby to cover the interior of the fixture. Access door 18 has an air inlet opening 24 and an air outlet opening 26 formed at opposite ends thereof. Air inlet opening 24 has an air grid or louver system 28 mounted in the opening in any convenient manner. An air filter 30 of conventional construction is mounted above, or rests on, louver structure 28 in order to remove dust particles and the like from air entering housing 12.

An enclosed air supply chamber 32 is located within housing 12 above air inlet opening 24. Air supply chamber 32 is defined by a front wall member 34 which extends transversely across the housing and by a top wall member 35. The remaining sides of the chamber are defined by the side walls and end wall 36 of housing 12.

A bulkhead wall 45 extends across housing 12 above chamber 32 to define a chamber 80 in the housing. Bulkhead 45 has an air outlet opening 38 formed therein which is aligned with the tangential air outlet opening 40 of a scroll type blower 42. The blower 42 is generally of conventional construction and includes a scroll housing 44 which has a tangentially arranged air outlet arm whose free end defines opening 40. Blower 42 is mounted on the top wall 35 of chamber 32 and is driven by a motor 48 which operates a scroll wheel 50 within housing 44 in a conventional manner in order to draw air through the inlet opening 24, louvers 28 and filter 30 into the air inlet chamber 32. The air is then drawn into the blower through the aligned circular openings 37, 39 formed in top wall 35 and housing 44. It has been found that the height of the air chamber 32 should be at least one half the diameter of the blower wheel 50 in order to reduce air turbulence and provide the most efficient operation for the motor. The air drawn into the housing by the motor is expelled through the tangential discharge arm 46 into the interior of the housing.

Preferably the openings 37, 39 are covered by a light trap 47 mounted on the underside of wall 35 in any convenient manner. The light trap blocks UV light from escaping chamber 80 through the blower. It also serves as a finger guard for the wheel of the blower when door 18 is opened.

As noted, discharge opening 40 of blower 42 communicates with the interior chamber 80 of housing 10 through the opening 38 formed in bulkhead 45. Wall 45 extends transversely of the housing and prevents any air flow back towards the motor and thereby promotes uniform air flow in the housing.

An air distribution system 60 is located within housing 12 downstream of blower 42 in order to produce a uniform cross-sectional air flow within the remainder of the housing. Air distribution system 60 includes a first screen 62 and a second screen 64. Screen 62 has a plurality of geometrically shaped openings (e.g. hexagonal or circular shaped) formed therein throughout its surface area in any convenient manner. Screen 64 has a plurality of geometrically shaped openings, circular openings, formed therein throughout its surface area. It has been found that screens 62, 64 should be spaced from one another by a distance equal approximately to 0.10× the cross sectional area of the chamber. With a 12"×12" cross sectional chamber area, the spacing D between the screens should be about 1.25–1.50 inches. The screens are mounted in housing 12 in any convenient manner.

In the illustrative embodiment the lower edges 66 of screens 62, 64 are mounted on a support structure 68 which extends transversely in the housing. Support 68 blocks any air flow therethrough so that all of the air flow from blower 42 flows through the screens. Support structure 68 also provides support for the sockets 70 of the UV system described hereinafter.

Preferably the open area of the screen 62 is about 72% while the open area of screen 64 is about 48%. It has been found that this relationship promotes uniform air velocities and flow in chamber 80. In addition, the air holes in screen 64 may be selectively blocked, as necessary, to promote the desired uniform air flow.

In addition to the spacing between the screens, it has been found that in order to ensure uniform air distribution through the system, with a minimum of turbulence, the first screen 62 should be spaced a predetermined distance from the air discharge opening 40 of the blower. In this regard, it has been found that this distance D' should be at least equal to one diameter of the wheel 50 in blower 42. These dimensions ensure that air flowing out of the distribution system 60 will flow smoothly and uniformly through the chamber portion 80 defined between the screens and the end wall 82 of the housing.

Chamber 80 includes the UV system 84 of the invention. In this embodiment of the invention, with a 1' wide housing, four elongated cylindrical UV-C lamps 85 are utilized. Preferably these bulbs have an intensity of 142 µW/cm$^2$ measured at 1 meter in a black box and they emit UV-C irradiation at the major germicidal wave length of 254 nm. In order to ensure good inactivation of airborne particles, it is important that the lamp spacing be equal across the width of chamber 80. It has been found that the spacing should be between 2 and 4 inches O. C. and preferably approximately 2 inches O. C. It has been found that the effectiveness of bacterial inactivation of these lamps decreases with distance from the lamps. Therefore, according to the present invention, the air is caused to flow uniformly between the equally spaced lamps to insure maximum inactivation of bacteria.

In the illustrative embodiment, the lamps 85 are positioned at an angle to the direction of air flow in order to maximize the UV output of the lamps and the residence time of the bacteria relative to the bulbs.

Lamps 85 used in the fixture of the invention are controlled through ballasts 90 mounted on the top wall 91 of the housing in any convenient manner. Preferably, one ballast is associated with two lamps. These ballasts are conventional electronic ballasts which serve to increase UV outlet of the lamps, while lowering energy consumption. Such ballasts have previously been used with florescent light fixtures, but have been found by the inventors to be suitable for use with UV lamps as well. The use of electronic ballasts allow the lamps to run at higher energy levels and produce increased bactericide activity.

The use of electronic ballasts also reduces the heat generated within the fixture. It has been found that the level of radiant energy produced by UV lamps is temperature dependent and that the efficiency of operation of the UV lamps decreases when temperatures deviate from the 60° to 80° F. range. Since electronic ballasts produce substantially less heat than conventional ballasts they reduce the heat problem associated with conventional ballasts.

Typically, UV lamps operate at very high voltages, particularly for starting purposes. As a result, such lamps are usually used with high output sockets having built in cut-off switches which ensure that the lamps cannot be activated without the lamps being securely seated in their sockets. This avoids possible arcing during installation of the lamps. Such sockets are very expensive. However, according to the present invention, the need for such expensive sockets has been eliminated. In accordance with the present invention a safety cut-off switch 100 is provided in housing 12 adjacent door 18. The safety cut-off switch, which can be of a conventional contact type, engages a finger 101 which projects upwardly from door 18 when closed and allows current to flow to the ballasts and to the motor 48 of the blower. However, when the door is opened, for example for purposes of replacing the lamps or replacing the filters, current to the motor and the lamps is automatically cut-off, thus eliminating the need for high output sockets as well as for the normally required finger guard over the opening 39 of the blower housing 44.

Additionally felt gaskets 103 or the like are located at approximate positions between door 18 and adjacent the guides of the inlet and outlet opening to ensure against escape of UV light through the door when it is closed.

An air outlet chamber 110 is formed in housing 10 above air outlet opening 26. This air outlet chamber is defined by a baffle 112 which extends transversely across the width of the housing. The open upper end 114 of chamber 110 is closed by a light trap 116 (FIG. 5) which permits air to flow from housing chamber 80 into the air discharge chamber 110 while preventing any UV radiation from passing out of chamber 80.

Chamber 80 has all of its internal surfaces covered with a reflective material, such as, for example, specular aluminum, to increase the efficiency of use of the UV radiation formed by the bulbs. However, it is desirable not to have any of that radiation escape from the housing. That is prevented by light trap 116. As shown in FIG. 5, light trap 116 is formed from economically manufactured stamped metal elements 120, 121 and 122 which have transverse vanes 124 stamped therein in order to define air openings 126. (A fourth stamped element can be used if desired.) The fins or vanes 124 of elements 120–122 each have a width dimension W of any desired length. However, to avoid having UV radiation pass from chamber 80 to chamber 110, the bases 128 of the fins in element 120 are offset laterally from the bases 130 of the fins in element 121 and the bases 131 of element 122 are offset from the bases 130 of fins 121 by the dimension of 0.5 W. In addition, the angle ∞ formed by the vanes is selected to be between 35° and 45°. This arrangement assures that no UV radiation can pass out of chamber 80.

Air outlet opening 26 includes a diffuser 132 formed with a plurality of louvers, corresponding generally to the louver arrangement 28 described above for the air inlet opening to the housing. In addition, a final air filter 134 of conventional construction may be mounted above the air outlet louver structure 132. This filter may also be a conventional charcoal filter if desired.

In this embodiment of the invention wherein the housing 10 has a 1' by 1' by 4' dimension, the air flow rate generated by blower 42 is about 250 cubic feet per minute (cfm). In this context, the range of air flow permitted by motor variations can be between 230 and 280 cfm per minute. This air flow rate, with the dimensions of the housing, produces a residence time for airborne bacteria in the chamber 80 of about 0.65 seconds. This assures a desirable air exchange rate in the room in which the unit is used, while at the same time producing maximum bacteriocidal action.

In this embodiment of the invention, blower 42 is illustrated at the air inlet side of the housing. However, if desired, the blower can be arranged at the air outlet side of the housing to draw air from the inlet across the lamps where the bacteria is killed, before entering the blower. This avoids the possibility of bacteria becoming entrapped in the blower component.

Figure 6A:
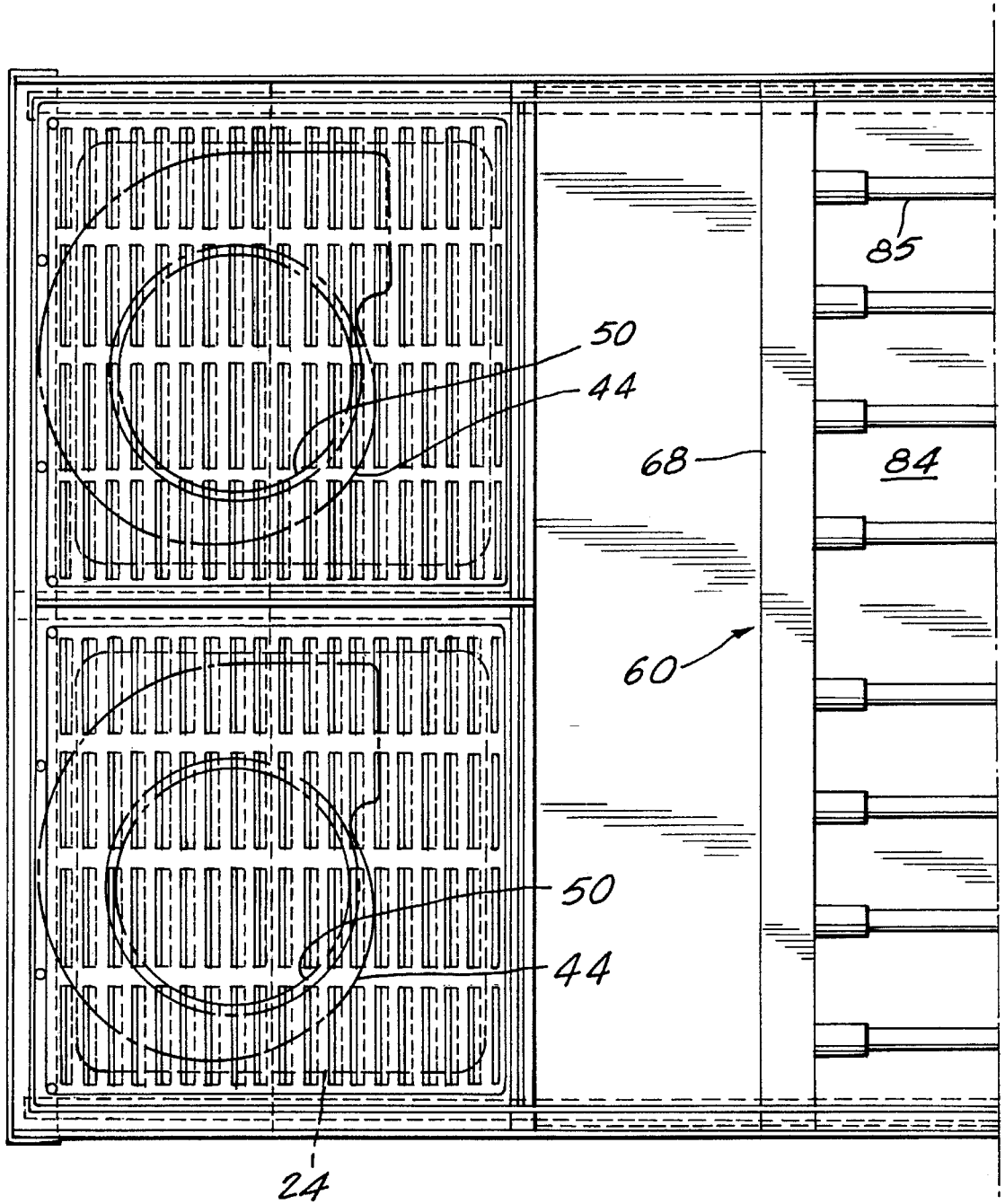
FIG. 6 is a bottom view similar to FIG. 4 of another embodiment of the invention wherein the fixture is 2 feet wide.
Figure 6B:
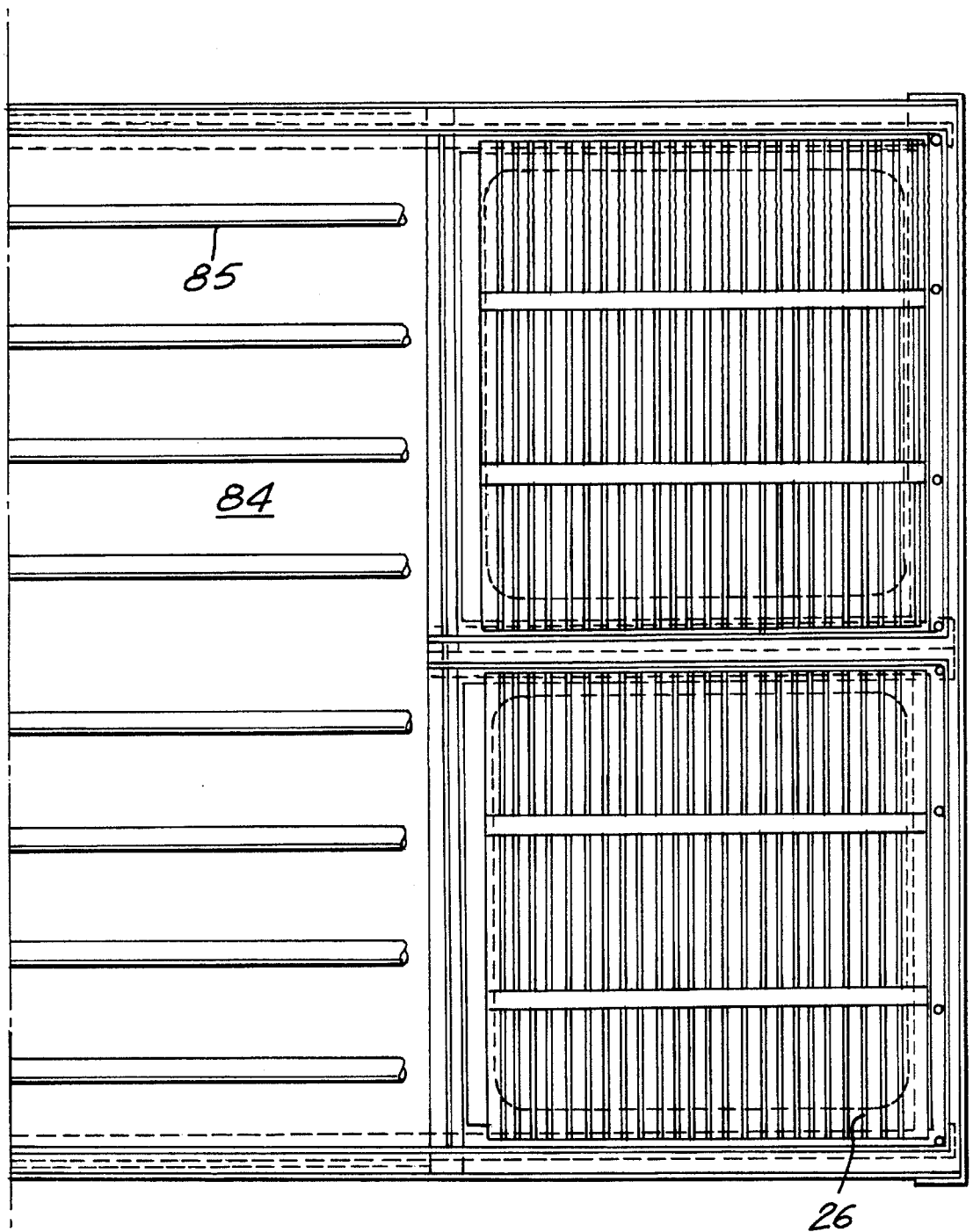

FIG. 6 illustrates a larger sized disinfectant device according to the present invention having dimensions of 1' in height, 2' in width and 4' in length. This embodiment is of similar construction as the 1'×1'×4' device disclosed above, and simply includes a second 1'×1'×4' unit in the same housing. There of course is no longitudinal separating wall between the two units.

Because of the larger volume of the unit of this embodiment the two blowers, together produce air flow rates of about 500 cfm, i.e. between 450 and 550 cfm. Otherwise the two devices are identical.

Figure 7:
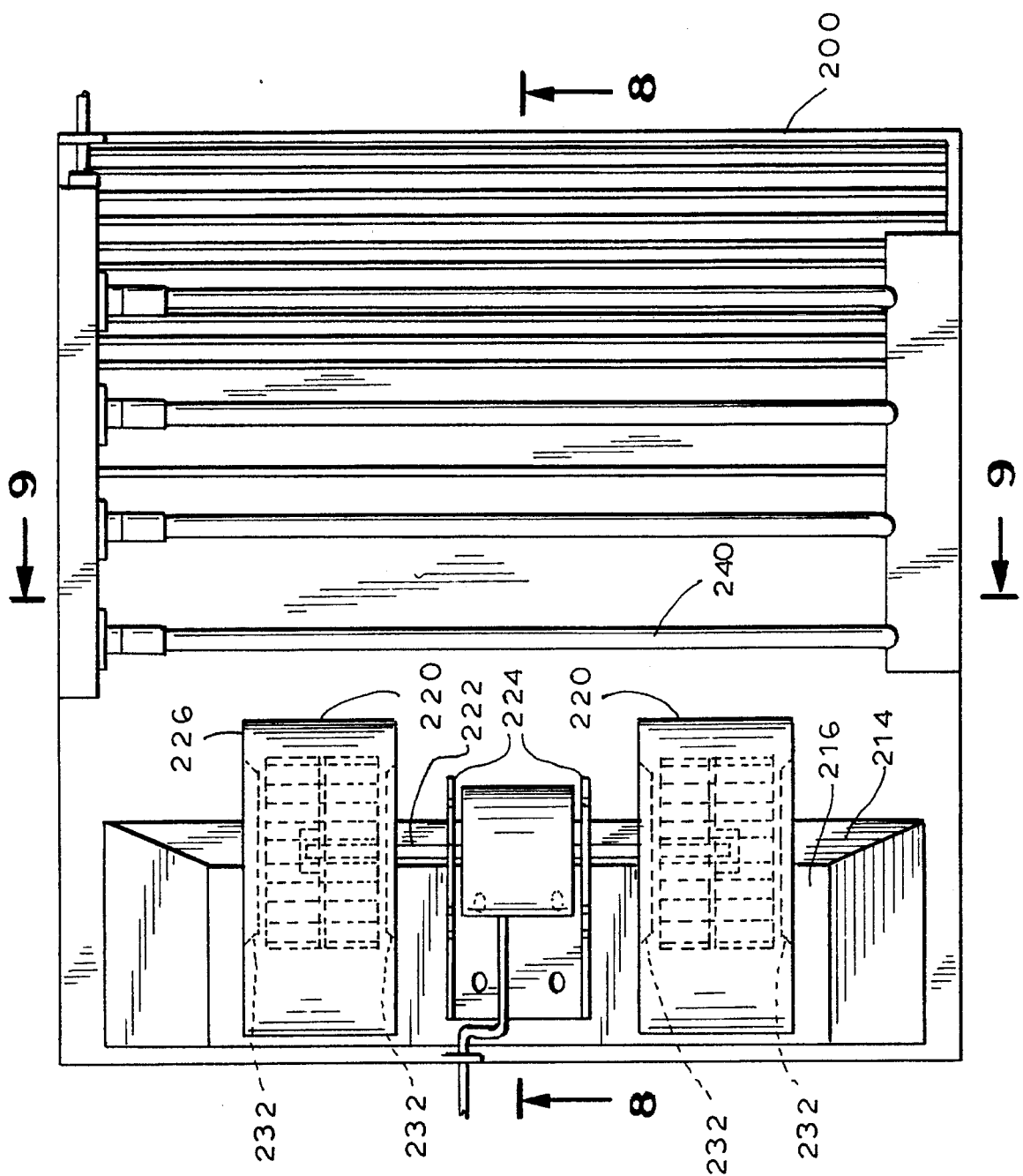
FIG. 7 is a top view (with the top wall removed) of another embodiment of the present invention.
Figure 8:
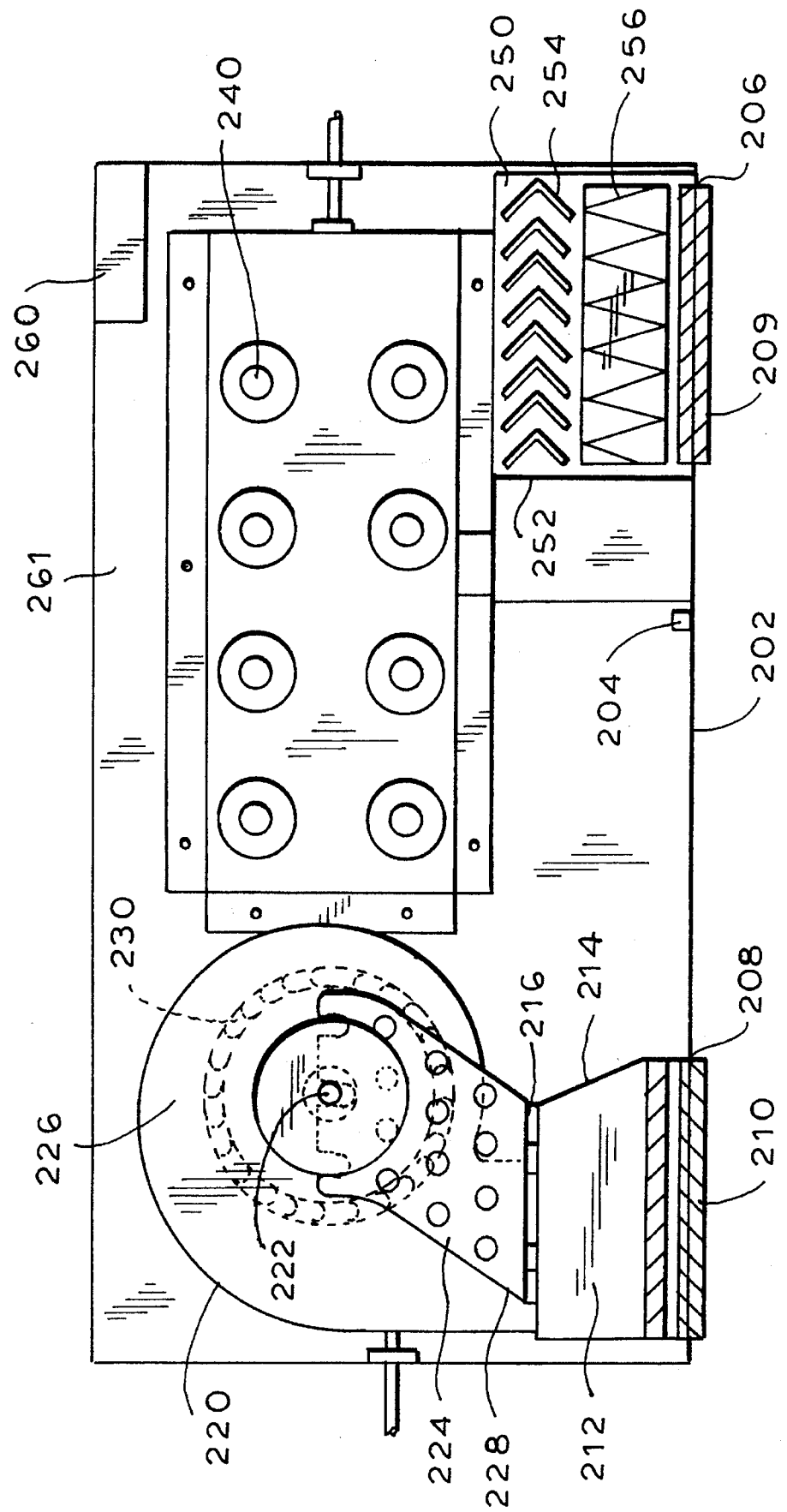
FIG. 8 is a sectional view taken along line 8—8 of FIG. 7.
Figure 9:
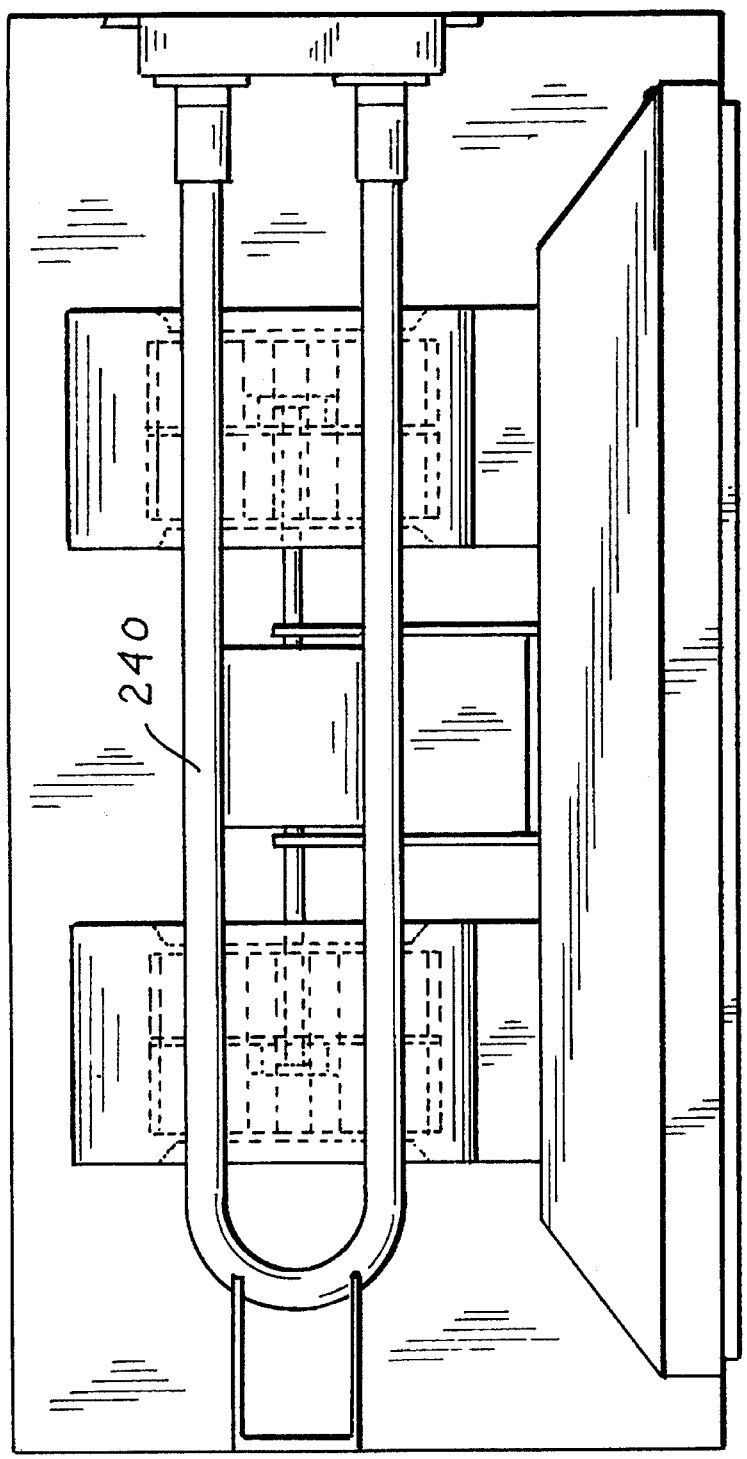
FIG. 9 is a sectional view taken along line 9—9 of FIG. 7.

FIGS. 7–9 illustrate yet another embodiment of the present invention using a 1' by 2' by 2' size housing 200 and in which the air is drawn across the UV-C lamps before entering the blower.

In this embodiment housing 200 has a bottom door 202 which is hinged to housing in any convenient manner in order to provide access of the interior of the housing, as described above with the embodiment of FIG. 1. Door 202 has a shut off switch 204 associated therewith to cut off power to the blowers and lamps of this embodiment when the door is open.

Access door 202 has an air inlet opening 206 and air outlet opening 208 formed therein. These openings contain decorative air louvers 209, 210, mounted in the door in any convenient manner. An air outlet plenum 212 is formed in housing 200 above air outlet opening 208 by a transverse wall 214 and an upper wall 216.

In this embodiment of the invention two scroll type blowers 220 are provided which have a common shaft 222 that is supported in support arms 224 mounted on wall 216. Each blower has a housing 226 with a tangential air outlet section 228 formed therein. These air outlets communicate through air openings in wall 216 in order to allow air to flow from the blowers into plenum 212 and out opening 208. Each blower has a conventional wheel construction 230 secured to shaft 222 to draw air into the blower housings from the interior of housing 200, thereby causing room air to enter inlet 206. Blower housings 226 have opposed axial air inlet openings 232 formed therein on opposite sides. By providing the motors with opposed air inlet openings, the air flow rate produced within the confined housing is such as to produce a non-turbulent uniform cross-sectional air flow from the air inlet opening 206 to the blowers.

In this embodiment of the invention, U-shaped UV-C lamps 240 are utilized. Four such bulbs are illustrated with the spacing therebetween being between 2 and 4 inches. As a result, all of the air passes within 2"–3" of a UV lamp, in this case-multiple times, in order to produce improved bacteriocidal action. Here again, all of the interior surfaces of the housing are formed to be reflective, for example, by the use of specular aluminum.

An air inlet plenum 250 is formed in housing 200 by a bulkhead 252 above air inlet opening 206. A light trap 254 is mounted in the plenum to prevent UV radiation from exiting housing 200. This light trap can be in the form previously described or can take any other known light trap configuration as desired. In addition, if desired, a filter, such as a charcoal filter 256, can be positioned in the chamber 252 above louver system 209. In this embodiment of the invention the ballasts 260 which control power to the UV lamps are also located on the top wall 261 of the housing in any convenient manner.

Although illustrative embodiments of the present invention have been described here in detail, it is to be understood that the invention is not limited to those precise embodiments and that various changes and modifications can be effected therein without departing from the scope or spirit of this invention.

What is claimed is:

1. An air disinfection unit comprising a housing having air inlet and air outlet openings formed therein; selectively operable means in said housing for passing air through the housing in an air stream from said inlet to said outlet opening at a predetermined air flow rate; means in said housing between said air inlet and outlet openings for producing UV-C irradiation; said means comprising a plurality of UV lamps having elongated UV-C producing portions located in closely spaced relation to each other at a distance of between 2" to 4" O. C.; said UV-C producing portions being positioned directly in said air stream produced by said selectively operable means for passing air whereby all air flows passes over and between said lamps at a distance of no more than about 2"–3" from a lamp; said lamps being capable of producing UV-C irradiation at a wavelength of about 254 nm and having an intensity of about 142 µW/cm$^2$; said housing having a predetermined volume selected such that airborne bacteria remain in the housing for a residence time of between 0.5 and 1.0 seconds; and means in said housing for producing substantially uniform air flow in said housing across and between said lamps comprising a pair of spaced air screens located in the air stream produced by said selectively operable means, upstream of said lamps in the direction of air flow.

2. An air disinfection unit as defined in claim 1 wherein said means for passing air through the housing comprises means for producing an air flow rate of about 250 standard cubic feet per minute.

3. An air disinfection unit as defined in claim 1 wherein said predetermined volume is selected such that the air residence time is about 0.65 seconds.

4. An air disinfection unit as defined in claim 3 wherein the dimensions of said housing are 1'×1'×4' and the air flow rate is between 230 and 280 cfm.

5. An air disinfection unit as defined in claim 3 wherein the dimensions of said housing are nominally 1'×2'×4'.

6. An air disinfection unit as defined in claim 3 wherein the dimensions of said housing are 1'×2'×4' and the air flow rate is between 475 and 525 cfm.

7. A disinfection unit as defined in claim 1 wherein said pair of screens are spaced from each other a longitudinal distance defined as approximately 0.1 times the cross-sectional area of the housing.

8. A disinfection unit as defined in claim 7 wherein said pair of screens include a first screen having geometrically shaped openings formed therein and a second screen, downstream of said first screen in the direction of air flow, also having geometrically shaped openings formed therein.

9. A disinfection unit as defined in claim 1 wherein said means for passing air through the housing comprises at least one scroll type blower having a central turbine wheel and a central air inlet opening; said blower having a tangential air outlet opening and said pair of screens being spaced from said tangential air outlet opening by a distance equal to about one diameter of the wheel.

10. A disinfection unit as defined in claim 9 including an air inlet chamber positioned over the air inlet opening of said housing, said blower being mounted on said inlet chamber above the air inlet opening of the housing by a distance equal to approximately ½ the blower wheel diameter.

11. A disinfection unit as defined in claim 1 including a light trap positioned on the air outlet opening of the housing.

12. A disinfection unit as defined in claim 11 wherein said light trap comprises at least one pair of opposed frames having angular fins formed therein and extending towards the fins of the other frame; said fins having a width W, with the bases of the fins on each frame being offset by the dimension 0.5 W.

13. A disinfection unit as defined in claim 12 wherein said fins are positioned at an angle of between 35° and 45° to the plane of their respective frames.

14. A disinfection unit as defined in claim 1 wherein said lamps are straight tubes.

15. A disinfection unit as defined in claim 1 wherein said housing has an access opening formed therein and a movable door covering said access opening; and switch means in said housing for interrupting power to said lamps when the door is moved away from the access opening.

16. A disinfection unit as defined in claim 15 including electronic ballasts for energizing said lamps.

17. A disinfection unit as defined in claim 16 wherein said ballasts are located downstream of said lamps.

18. A disinfection unit comprising a housing having air inlet and air outlet openings formed therein; selectively operable means in said housing for passing air through the housing in an air stream from said inlet to said outlet opening at a predetermined air flow rate; means in said housing between said air inlet and outlet openings for producing UV-C irradiation; said means comprising a plurality of UV lamps having elongated UV-C producing portions located in closely spaced relation to each other at a distance of between 2" to 4" O. C.; said UV-C producing portions being positioned directly in said air stream produced by said selectively operable means for passing air whereby all air flows pass over and between said lamps at a distance of no more than about 2"–3" from a lamp; said lamps being capable of producing UV-C irradiation at a wavelength of about 254 nm and having an intensity of about 142 µW/cm$^2$; said housing having a predetermined volume selected such that airborne bacteria remain in the housing for a residence time of between 0.5 and 1.0 seconds; and means in said housing for producing substantially uniform air flow in said housing across and between said lamps; said means for passing air through the housing comprising a pair of scroll type blowers each having a blower housing and a central turbine wheel, said blower housings each having a pair of axial air inlet openings and a tangential air outlet opening; said air inlet openings in said blower housings defining said means for producing substantially uniform cross-sectional air flow in the enclosure across and between said lamps.

19. A disinfection unit as defined in claim 18 wherein said lamps are generally U shaped.

20. A disinfection unit comprising a closed housing having a lower access door movably mounted thereon, said access door having spaced air inlet and air outlet openings formed therein, selectively operable blower means associated with one of said openings for drawing air into and through said housing in an air flow stream from said air inlet opening to said air outlet opening at a predetermined air flow rate; a plurality of elongated UV-C irradiation lamps mounted in said housing between said inlet and outlet openings for producing UV-C irradiation, said lamps being positioned in closely spaced relation to each other at distances of between 2" to 4" O. C. transversely in said air flow stream in the housing whereby all air flows pass the lamps at a distance of no more than 3" from a lamp; said lamps producing UV-C irradiation at a wavelength of about 254 nm and having an intensity of about 142 µW/cm$^2$; said housing having a predetermined volume selected such that airborne bacteria remain in the housing for a residence time of between 0.5 and 1.0 seconds; and means in the housing for producing substantially uniform air flow in the housing through the lamps comprising a pair of spaced air screens located in the housing in the air stream produced by said selectively operable means upstream of the lamps in the direction of air flow and transverse to the direction of air flow said pair of screens being spaced from each other a longitudinal distance defined as 0.1 times the cross-sectional area of the housing and including a first screen having geometric openings formed therein and a second screen, upstream of said first screen having geometric openings formed therein.

21. An air disinfection unit as defined in claim 20 wherein said predetermined volume is selected such that the air residence time is about 0.65 seconds.

22. A disinfection unit as defined in claim 20 wherein said blower means is located upstream of said screens in the direction of air flow and adjacent said air inlet opening.

23. A disinfection unit as defined in claim 22 wherein said blower means comprises at least one scroll type blower having a central turbine wheel and a central air inlet opening; said blower means having a tangential air outlet opening and said pair of screens being spaced from said outlet opening by a distance equal to about one diameter of the turbine wheel.

24. A disinfection unit as defined in claim 23 including an air inlet chamber positioned over the air inlet opening of said housing, said blower being mounted on said inlet chamber above the air inlet opening of the housing by a distance equal to ½ the blower wheel diameter.

25. A disinfection unit as defined in claim 24 including a light trap positioned on the air outlet opening of the housing.

26. A disinfection unit as defined in claim 25 wherein said light trap comprises at least one pair of opposed frames having angular fins formed therein and extending towards the fins of the other frame; said fins having a width W, with the bases of the fins on each frame being offset by the dimension 5 W.

27. A disinfection unit as defined in claim 26 wherein said fins are positioned at an angle of between 35° and 45° to the plane of their respective frames.

28. A disinfection unit as defined in claim 24 including cut off switch means in said housing for interrupting power to said lamps and blower when the door is moved away from the access opening.

29. A disinfection unit as defined in claim 24 wherein said housing has an access opening formed therein and said access door covers said access opening; and switch means in said housing for interrupting power to said lamps when the door is moved away from the access opening.

30. A disinfection unit as defined in claim 24 wherein the interior surfaces of said housing have light reflective surfaces.

31. A disinfection unit comprising a closed housing having a lower access door movably mounted thereon, said access door having spaced air inlet and air outlet openings formed therein, selectively operable blower means associated with one of said openings for drawing air into and through said housing in an air flow stream from said inlet to said outlet opening at a predetermined air flow rate; a plurality of elongated UV-C irradiation lamps mounted in said housing between said inlet and outlet opening for producing UV-C irradiation, said lamps being positioned in closely spaced relation to each other at distances of between 2" to 4" O. C. transversely in said air flow stream in the housing whereby all air flows passes the lamps at a distance of no more than 2"–3" from a lamp; said lamps being capable of producing UV-C irradiation at a wavelength of about 254 nm and having an intensity of about 142 µW/cm$^2$; said housing having a predetermined volume selected such that airborne bacteria remain in the housing for a residence time of between 0.5 and 1.0 seconds; said blower means comprising a pair of scroll type blowers each having a blower housing including a tangential air outlet opening and a pair of axially located air inlet openings, said blowers being positioned in axial alignment to draw air from the air inlet opening of the housing through the housing to the blower means with a substantially uniform cross-section air flow in the housing across and between the lamps.

32. An air disinfection unit as defined in claim 31 wherein said housing volume is selected such that the air residence time is about 0.65 seconds.

33. A disinfection unit as defined in claim 32 including a light trap positioned on the air inlet opening of the housing.

34. A disinfection unit as defined in claim 31 wherein said lamps are generally U shaped.

35. A disinfection unit as defined in claim 34 including cut off switch means in said housing for interrupting power to said lamps and blower when the door is moved away from the housing.

36. A disinfection unit as defined in claim 35 including electronic ballasts for energizing said lamps.

37. A disinfection unit as defined in claim 36 wherein the interior surfaces of said housing have light reflective surfaces.

38. The method of disinfecting air from airborne bacterial comprising the steps providing an enclosure having UV sources, passing air through an enclosure at a predetermined air flow rate, maintaining a substantially uniform air flow in said enclosure across and between said light sources, exposing the uniform air flow in the enclosure to UV-C irradiation at a wavelength of about 254 nm, providing the irradiation from UV light sources having an intensity of 142 µW/cm$^2$ and maintaining the airborne bacteria in the enclosure for a residence time of about 0.65 seconds to ensure effective disinfection of the air.

39. The method as defined in claim 38 wherein said airflow rate is about 275 cfm.

40. The method as defined in claim 38 wherein said airflow rate is between 230 and 280 cfm.

41. The method as defined in claim 38 wherein the airflow rate is between 475 and 525 cfm.

42. The method as defined in claim 38 wherein said UV light sources are spaced apart no more than 2"–3" o.c.

* * * * *